United States Patent [19]

Del Pesco et al.

[11] Patent Number: 4,461,676
[45] Date of Patent: Jul. 24, 1984

[54] PROCESS FOR REFINING TETRAHYDROFURAN

[75] Inventors: Thomas W. Del Pesco; Richard H. Goldbaum, both of Wilmington, Del.

[73] Assignee: E. I. Du Pont De Nemours and Company, Wilmington, Del.

[21] Appl. No.: 394,119

[22] Filed: Jul. 1, 1982

[51] Int. Cl.³ .................... B01D 3/34; C07D 307/08
[52] U.S. Cl. ........................................ 203/29; 203/32; 203/37; 549/429
[58] Field of Search .................. 549/429; 203/29, 32, 203/33, 36, 37

[56] References Cited

U.S. PATENT DOCUMENTS

| | | | |
|---|---|---|---|
| 2,867,651 | 1/1959 | Wise | 203/32 |
| 3,860,520 | 1/1975 | Lindemuth et al. | 203/29 |
| 3,980,672 | 9/1976 | Tomomatsu | 549/429 |
| 4,257,961 | 3/1981 | Coates | 549/429 |
| 4,348,262 | 9/1982 | Stock | 549/429 |

FOREIGN PATENT DOCUMENTS 49-30353  3/1974  Japan ..................... 549/429

*Primary Examiner*—Wilbur L. Bascomb, Jr.

[57] ABSTRACT

The level of aldehyde and ketone impurities in tetrahydrofuran can be significantly reduced by bringing the tetrahydrofuran into contact with sodium borohydride and then separating the modified impurities and the tetrahydrofuran.

3 Claims, No Drawings

PROCESS FOR REFINING TETRAHYDROFURAN

DESCRIPTION OF THE INVENTION

Technical Field

This invention relates to a process for refining tetrahydrofuran (THF). It is more particularly directed to a process for removing aldehyde and ketone impurities from THF.

Background and Summary of the Invention

One of the many uses for THF is as a monomer in the preparation of poly(tetramethylene) ether glycol (PTMEG). In the product-washing stage of that preparation, a stream is commonly formed from which THF can be regenerated. It would obviously be desirable to recover this THF so that it could be recycled to the polymerization or used for other purposes.

Unfortunately, the THF formed in this way may contain as much as 2000 ppm of aldehyde and ketone impurities, which interfere with the THF's subsequent uses and which should therefore be removed.

It has now been found that these aldehyde and ketone impurities can be conveniently and efficiently removed from THF according to the invention by bringing the THF containing the impurities (crude THF) into contact with sodium borohydride. This converts the aldehydes and ketones to the corresponding alcohols and the borohydride to sodium metaborate, both of which are then removed from the THF to give a product in which the aldehyde and ketone content may be reduced to a level as low as 25 ppm.

The process of the invention is not confined to treatment of crude THF recovered from the PTMEG process, but may be used to treat any THF stream containing aldehyde and ketone impurities, from whatever source.

Detailed Description of the Invention

The aldehyde and ketone impurities in the crude THF processed according to the invention are commonly propionaldehyde, i-butyraldehyde, n-butyraldehyde, acetone and methylethyl ketone.

The sodium borohydride used in the process of the invention can be of any grade or variety obtainable in the marketplace. The borohydride is unstable under acidic conditions and so is ordinarily supplied as a 10-14% by weight solution in 30-50% aqueous NaOH, in which form it is preferably used.

Crude THF is refined according to the invention by bringing it into contact with the borohydride, either batchwise or continuously.

In the batch mode, the amount of borohydride to be used is calculated by first determining the aldehyde and ketone content of the crude THF by gas chromatography. An excess over the stoichiometric amount of borohydride, (based on the aldehyde and ketone content) preferably as a solution in aqueous sodium hydroxide, is then added to the THF, with stirring.

The pH of the resulting mixture should be kept in the range 8-14. In the preferred embodiment, in which a borohydride/NaOH solution is used, this pH range is obtained automatically.

The temperature of the reaction mixture is held within the range of 20° C. to its reflux temperature, ordinarily about 64° C. Reflux temperature is preferred.

The length of time the THF is thus treated depends upon the temperature used and the amount of aldehydes and ketones to be removed. With the typical crude THF, the aldehyde and ketone content can in most cases be brought to a satisfactory level in about 30 minutes.

The resulting converted aldehydes and ketones, and the resulting sodium metaborate, may then be separated from the THF by conventional chemical engineering techniques, ordinarily and preferably distillation, using customary equipment operated under conditions well known to those skilled in the art.

In the continuous mode, the proper amount of sodium borohydride is continuously added to a stream of crude THF in a reaction zone, from which the THF is then continuously fed to a distillation train or other apparatus in which the converted aldehydes and ketones and the sodium metaborate are removed. The conditions in the reaction zone are otherwise the same as those used in the batch mode, with dwell times of the THF in the reaction zone of up to about 30-40 minutes.

THF refined according to the invention is suitable for most purposes, and can in fact be pure enough to be recycled to the polymerization train from which it was taken.

EXAMPLE (Best Mode)

Crude THF containing 88% by weight of THF and 12% by weight of water was analyzed by gas chromatography to determine the identity and concentration if its aldehyde and ketone impurities. The results are shown in the table.

Sixty parts by volume of the crude THF were then heated to its boiling point, 64° C., and held under reflux conditions, with stirring, while 0.2 part by volume of an aqueous solution containing 12% by weight of sodium borohydride and 40% by weight of sodium hydroxide was added to it.

After the THF had refluxed for 30 minutes, 1 part by volume of concentrated sulfuric acid was added to it to decompose any remaining unreacted sodium borohydride so that a reaction time could be defined.

Forty-five parts by volume of this THF were then distilled in a spinning band column, at a reflux ratio of 10/1. Distillation was stopped when 94% by volume of the THF had been taken off as the atmospheric THF/water azeotrope.

The aldehyde and ketone content of the resulting purified THF, as determined by gas chromatography, is shown in the table.

TABLE

| | Concentration in ppm | | | | | |
|---|---|---|---|---|---|---|
| | Propion-aldehyde | i-Butyr-aldehyde | n-Butyr-aldehyde | Acetone | Methyl-ethyl TAL | TO- |
| Crude THF | 108 | 486 | 678 | 14 | 800 | 2086 |
| Purfied THF | — | — | — | 1 | 25 | 26 |

We claim:

1. A process for removing aldehyde and ketone impurities from tetrahydrofuran, the process comprising
   (a) bringing the tetrahydrofuran into contact, under basic conditions, with an excess over the stoichiometric amount (based on the aldehydride and ketone content of the tetrahydrofuran) of sodium borohydride; and then
   (b) separating the resulting reaction products and the tetrahydrofuran.

2. The process of claim 1 wherein the separation in (b) is by distillation.

3. The process of claim 2 wherein the contacting in (a) is at a temperature of 20°-64° C. and at a pH of 8-14.

* * * * *